US011921057B2

(12) United States Patent
Aoki et al.

(10) Patent No.: US 11,921,057 B2
(45) Date of Patent: Mar. 5, 2024

(54) X-RAY IMAGING DEVICE

(71) Applicants: NATIONAL UNIVERSITY CORPORATION SHIZUOKA UNIVERSITY, Shizuoka (JP); ANSeeN Inc., Hamamatsu (JP)

(72) Inventors: Toru Aoki, Hamamatsu (JP); Katsuyuki Takagi, Hamamatsu (JP); Akifumi Koike, Hamamatsu (JP)

(73) Assignees: NATIONAL UNIVERSITY CORPORATION SHIZUOKA UNIVERSITY (JP); ANSEEN INC. (JP)

( * ) Notice: Subject to any disclaimer, the term of this patent is extended or adjusted under 35 U.S.C. 154(b) by 391 days.

(21) Appl. No.: 17/432,611

(22) PCT Filed: Feb. 26, 2019

(86) PCT No.: PCT/JP2019/007292
§ 371 (c)(1),
(2) Date: Aug. 20, 2021

(87) PCT Pub. No.: WO2020/174577
PCT Pub. Date: Sep. 3, 2020

(65) Prior Publication Data
US 2022/0196575 A1 Jun. 23, 2022

(51) Int. Cl.
*G01N 23/046* (2018.01)
*A61B 6/03* (2006.01)
*G01S 17/08* (2006.01)

(52) U.S. Cl.
CPC .......... *G01N 23/046* (2013.01); *A61B 6/032* (2013.01); *G01S 17/08* (2013.01); *G01N 2223/323* (2013.01)

(58) Field of Classification Search
CPC ......... A61B 17/1703; A61B 5/05; A61B 5/00; A61B 5/0048; A61B 5/0093; A61B 5/066;
(Continued)

(56) References Cited

U.S. PATENT DOCUMENTS

2002/0114426 A1* 8/2002 Polkus ................. A61B 6/4233
378/207
2007/0086570 A1 4/2007 Spahn ........................ 378/117
(Continued)

FOREIGN PATENT DOCUMENTS

CN 104306009 A 1/2015
CN 104364824 A 2/2015
(Continued)

OTHER PUBLICATIONS

Office Action dated Apr. 19, 2022 in counterpart Japanese Application No. 2021-501428.
(Continued)

*Primary Examiner* — Don K Wong
(74) *Attorney, Agent, or Firm* — OSTROLENK FABER LLP

(57) ABSTRACT

An X-ray imaging device that includes an X-ray source, an X-ray sensor that acquires intensity information of X-rays, a distance sensor that obtains distance information to a surface of an imaging object, and an information processing device that obtains imaging information by using the intensity information and the distance information. The information processing device includes an extraction unit that extracts information used in generation of the imaging information from the intensity information by using at least the distance information, and a reconstruction unit that generates the imaging information by using the intensity information.

3 Claims, 12 Drawing Sheets

(58) Field of Classification Search
CPC . A61B 1/00174; A61B 5/0033; A61B 8/4245; A61B 8/463; A61B 8/5292; G06T 1/00; G01N 23/046; G01N 21/4795; G01N 21/8851; G01N 2223/1016; G01N 2223/3308; G01N 2223/04; G01N 2223/401

See application file for complete search history.

(56) References Cited

U.S. PATENT DOCUMENTS

| | | | |
|---|---|---|---|
| 2011/0116695 A1 | 5/2011 | Wollenweber et al. | 382/131 |
| 2012/0020452 A1 | 1/2012 | Arakita et al. | 378/8 |
| 2013/0245461 A1 | 9/2013 | Maier-Hein et al. | 600/476 |
| 2014/0016750 A1 | 1/2014 | Kang et al. | 378/62 |
| 2015/0265219 A1 | 9/2015 | Feiweier et al. | |
| 2016/0310093 A1 | 10/2016 | Chen et al. | |
| 2018/0085082 A1 | 3/2018 | Kawano | |
| 2018/0333208 A1 | 11/2018 | Kotian et al. | |

FOREIGN PATENT DOCUMENTS

| | | |
|---|---|---|
| CN | 107456236 A | 12/2017 |
| JP | H06-90946 A | 4/1994 |
| JP | H06-269445 A | 9/1994 |
| JP | 2006-288472 A | 10/2006 |
| JP | 2007-082908 A | 4/2007 |
| JP | 2008-253765 A | 10/2008 |
| JP | 2009-273671 A | 11/2009 |
| JP | 2010-051337 A | 3/2010 |
| JP | 2011-101741 A | 5/2011 |
| JP | 2012-005695 A | 1/2012 |
| JP | 2012-040363 A | 3/2012 |
| JP | 2013-250742 A | 12/2013 |
| JP | 2015-079011 A | 4/2015 |
| JP | 2015-089452 A | 5/2015 |
| JP | 2015-130906 A | 7/2015 |
| JP | 2015-198824 A | 11/2015 |
| JP | 2017-148110 A | 8/2017 |
| TW | 201827014 A | 8/2018 |
| TW | 201907154 A | 2/2019 |

OTHER PUBLICATIONS

Office Action dated May 18, 2022 in counterpart Taiwanese Application No. 109104202.
Office Action dated Mar. 14, 2023 in counterpart Japanese Patent Application No. P2022-098897.
International Search Report dated May 28, 2019 in corresponding International Application No. PCT/JP2019/007292.
English Translation of the International Preliminary Report on Patentability (IPRP) dated Aug. 26, 2021 with a Notification from the International Bureau (Form PCT/IB/338) in corresponding PCT International Application No. PCT/JP2019/007292.
Extended European Search Report dated Sep. 5, 2022 in counterpart European Patent Application No. 19916559.8.

\* cited by examiner

X-RAY IMAGING DEVICE

CROSS-REFERENCE TO RELATED APPLICATIONS

The present application is a 35U.S.C. §§ 371 national phase conversion of International Application No. PCT/JP2019/007292, filed Feb. 26, 2019, the content of which is incorporated herein by reference. The PCT International Application was published in the Japanese language.

TECHNICAL FIELD

The present disclosure relates to an X-ray imaging device.

BACKGROUND ART

A radiation detector is widely used as means for non-destructively imaging internal information in a medical field, an industrial field, and the like. Patent Literature 1 to Patent Literature 4 disclose devices using radiation. Examples of a device using a radiation detector include computed tomography (CT). Patent Literature 1 to Patent Literature 3 disclose a technology relating to the computed tomography.

CITATION LIST

Patent Literature

Patent Literature 1: Japanese Unexamined Patent Publication No. 2017-148110
Patent Literature 2: Japanese Unexamined Patent Publication No. 2012-5695
Patent Literature 3: Japanese Unexamined Patent Publication No. 2011-101741
Patent Literature 4: Japanese Unexamined Patent Publication No. 2015-79011

SUMMARY OF INVENTION

Technical Problem

The computed tomography regards a state in which a relative positional relationship between an X-ray sensor and an imaging object does not vary during imaging as an ideal state. That is, when the relative positional relationship between the X-ray sensor and the imaging object does not vary, theoretically, an image having the highest resolution can be obtained. That is, performance of the X-ray sensor can be sufficiently exhibited. However, the relative positional relationship between the X-ray sensor and the imaging object during imaging varies due to several factors. Therefore, the performance of the X-ray sensor cannot be exhibited to the maximum.

Here, the present disclosure describes an X-ray imaging device capable of sufficiently drawing out performance of an X-ray sensor.

Solution to Problem

According to an aspect of the present disclosure, there is provided an X-ray imaging device that obtains imaging information indicating an internal structure of an imaging object by using intensity of X-rays transmitted through the imaging object. The X-ray imaging device includes: an X-ray source that emits the X-rays toward the imaging object; an X-ray intensity measurement unit that is disposed to face the X-ray source with the imaging object interposed therebetween, and obtains intensity information of the X-rays transmitted through the imaging object; a distance measurement unit that irradiates the imaging object with measurement light reflected from a surface of the imaging object, and obtains distance information to the surface of the imaging object by using the measurement light reflected from the surface of the imaging object; and an information processing unit that obtains the imaging information by using the intensity information and the distance information. The information processing unit includes an extraction unit that extracts information used in generation of the imaging information from a plurality of pieces of the intensity information by using at least the distance information, and an image generation unit that generates the imaging information by using the intensity information extracted in the extraction unit.

The information processing unit of the X-ray imaging device extracts information used in generation of the imaging information from the intensity information by using at least the distance information. The distance information represents a relative positional relationship between the X-ray intensity measurement unit and the imaging object. Accordingly, the information processing unit can extract information suitable for generation of the imaging information on the basis of the distance information. As a result, deterioration of the quality of the imaging information is suppressed, and thus performance of the X-ray intensity measurement unit can be sufficiently drawn out.

The extraction unit of the X-ray imaging device may include a distance difference acquisition unit that acquires a distance difference between first distance information acquired at a first timing and second distance information acquired at a second timing, a distance evaluation unit that evaluates whether or not the distance difference is within an allowable range, and outputs first permission information when the distance difference is within the allowable range, and a labelling unit that applies information indicating use for generation of the imaging information to the intensity information acquired at the second timing when the output of the distance evaluation unit is the first permission information. According to this configuration, intensity information suitable for generation of the imaging information can be appropriately extracted.

The distance evaluation unit of the X-ray imaging device may output first prohibition information when the distance difference is not within the allowable range, and the extraction unit may further include an intensity difference acquisition unit that acquires an intensity difference between first intensity information acquired at the first timing and second intensity information acquired at the second timing, an intensity evaluation unit that evaluates whether or not the intensity difference is within an allowable range, outputs second permission information when the intensity difference is within the allowable range, and outputs second prohibition information when the intensity difference is not within the allowable range, and an aspect evaluation unit that evaluates that a variation in a first aspect has occurred in the imaging object when the output of the distance evaluation unit is the first prohibition information and the output of the intensity evaluation unit is the second permission information, and evaluates that a variation in a second aspect has occurred in the imaging object when the output of the distance evaluation unit is the first prohibition information and the output of the intensity evaluation unit is the second prohibition information. According to this configuration, in the relative positional relationship between the X-ray intensity measurement unit and the imaging object, a variation aspect of the positional relationship can be determined.

The X-ray intensity measurement unit of the X-ray imaging device may acquire intensity distributions of the X-rays which are emitted from the X-ray source and are transmitted through the imaging object as the first intensity information and the second intensity information, and the aspect evaluation unit may determine that the first aspect is either a deformation of the imaging object or movement of the imaging object in correspondence with a comparison result between the intensity distribution indicated by the first intensity information and the intensity distribution indicated by the second intensity information. According to this configuration, in the relative positional relationship between the X-ray intensity measurement unit and the imaging object, the variation aspect of the positional relationship can be determined in more detail.

Advantageous Effects of Invention

According to the X-ray imaging device of the present disclosure, performance of the X-ray sensor can be sufficiently drawn out.

DESCRIPTION OF EMBODIMENTS

Figure 1:
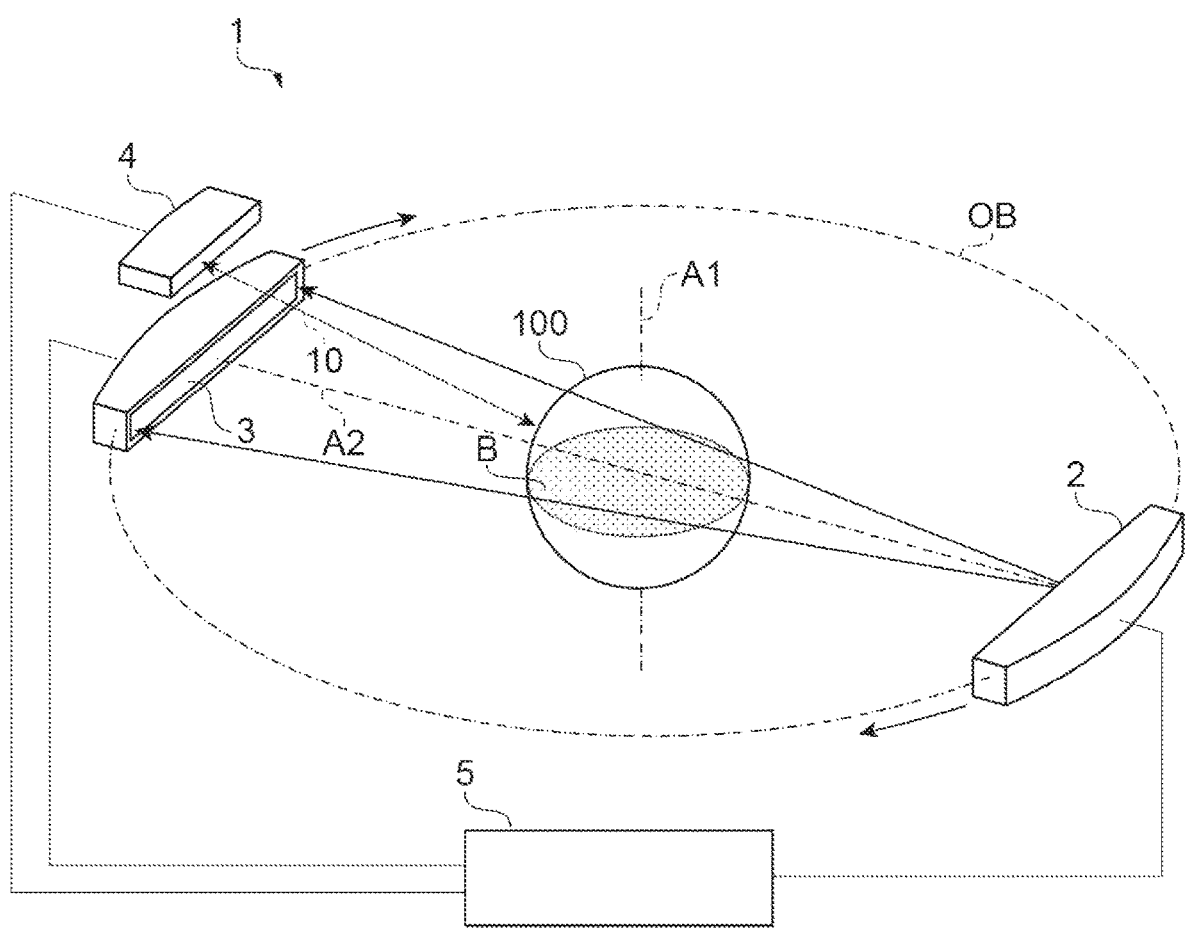
FIG. 1 is a perspective view illustrating a main configuration of an X-ray imaging device of a first embodiment.

Hereinafter, an X-ray imaging device of the present disclosure will be described in detail with reference to the accompanying drawings. The same reference numeral will be given to the same element in description of the drawings, and redundant description will be omitted.

First Embodiment

As illustrated in FIG. 1, an X-ray imaging device 1 obtains a reconstruction image as imaging information indicating an internal structure of an imaging object 100. In addition, the X-ray imaging device 1 obtains voxel data showing a three-dimensional internal structure of the imaging object 100 by using a plurality of reconstruction images. The X-ray imaging device 1 uses X-rays which are transmitted through the imaging object 100. The X-ray imaging device 1 includes an X-ray source 2, an X-ray sensor 3 (X-ray intensity measurement unit), a distance sensor 4 (distance measurement unit), and an information processing device 5 (information processing unit) as main configuration elements.

The X-ray source 2 emits X-rays toward the imaging object 100. The X-ray sensor 3 is disposed to face the X-ray source 2 with the imaging object 100 interposed therebetween. The X-ray sensor 3 acquires intensity information of the X-rays transmitted through the imaging object 100. The X-ray sensor 3 has a configuration in which the X-ray detection unit and a read-out circuit are stacked. The X-ray sensor 3 is a thin type, and thus, can be mounted at an ideal position. The X-ray source 2 and the X-ray sensor 3 revolve around an axial line A1. Due to the revolution, imaging information relating to an imaging plane B orthogonal to the axial line A1 can be obtained. In addition, the X-ray source 2 and the X-ray sensor 3 move in parallel with respect to the axial line A1. Due to the parallel movement, imaging information relating to a plurality of the imaging planes B can be obtained. When using the imaging information relating to the plurality of imaging planes B, the voxel data showing the three-dimensional internal structure of the imaging object 100 can be obtained.

The distance sensor 4 is disposed in the vicinity of the X-ray sensor 3. The distance sensor 4 is a two-dimensional sensor capable of performing real-time measurement. As the distance sensor 4, for example, time of flight (ToF) camera may be used. A relative position of the distance sensor 4 with respect to the X-ray sensor 3 is fixed. That is, the distance sensor 4 revolves around the axial line A1 in combination with the X-ray sensor 3. The distance sensor 4 obtains distance information up to a surface of the imaging object 100. The distance sensor 4 emits measurement light 10 to be reflected from the surface of the imaging object 100 toward the imaging object. In addition, the distance sensor 4 obtains distance information by using the measurement light 10 reflected from the surface of the imaging object 100.

The distance sensor 4 obtains distance information up to the imaging object 100 from the distance sensor 4. The distance information is used as distance information from the X-ray sensor 3 to the imaging object 100. For example, a revolution orbit OB of the X-ray source 2 and the X-ray sensor 3 is set. In addition, an axial line A2 that connects the X-ray source 2 and the X-ray sensor 3 is set. The axial line A2 overlaps the imaging object 100 and is orthogonal to the axial line A1. The distance sensor 4 may be disposed at a position overlapping the axial line A2 when viewed from a direction of the axial line A1. In addition, the distance sensor 4 may be disposed at a position overlapping the revolution orbit OB when viewed from the direction of the axial line A1. According to the disposition, the distance information from the distance sensor 4 to the imaging object 100 may be treated to be equivalent to the distance information from the X-ray sensor 3 to the imaging object 100.

Note that, disposition of the distance sensor 4 is illustrative only, and is not limited to the above-described disposition. The disposition of the distance sensor 4 is not particularly limited as long as the distance information from the X-ray sensor 3 to the imaging object 100 can be obtained. For example, the distance sensor 4 may be disposed on an X-ray detection plane of the X-ray sensor 3 having a stacked structure. According to this configuration, a size of a sensor capable of obtaining intensity information and distance information can be reduced.

The information processing device 5 obtains voxel data by using the intensity information and the distance information. The information processing device 5 is connected to the X-ray source 2, the X-ray sensor 3, and the distance sensor 4 in a wired or wireless manner. For example, the information processing device 5 acquires intensity information relating to X-rays received by the X-ray sensor 3 from the X-ray sensor 3. In addition, the information processing device 5 acquires distance information from the distance sensor 4.

Figure 2:
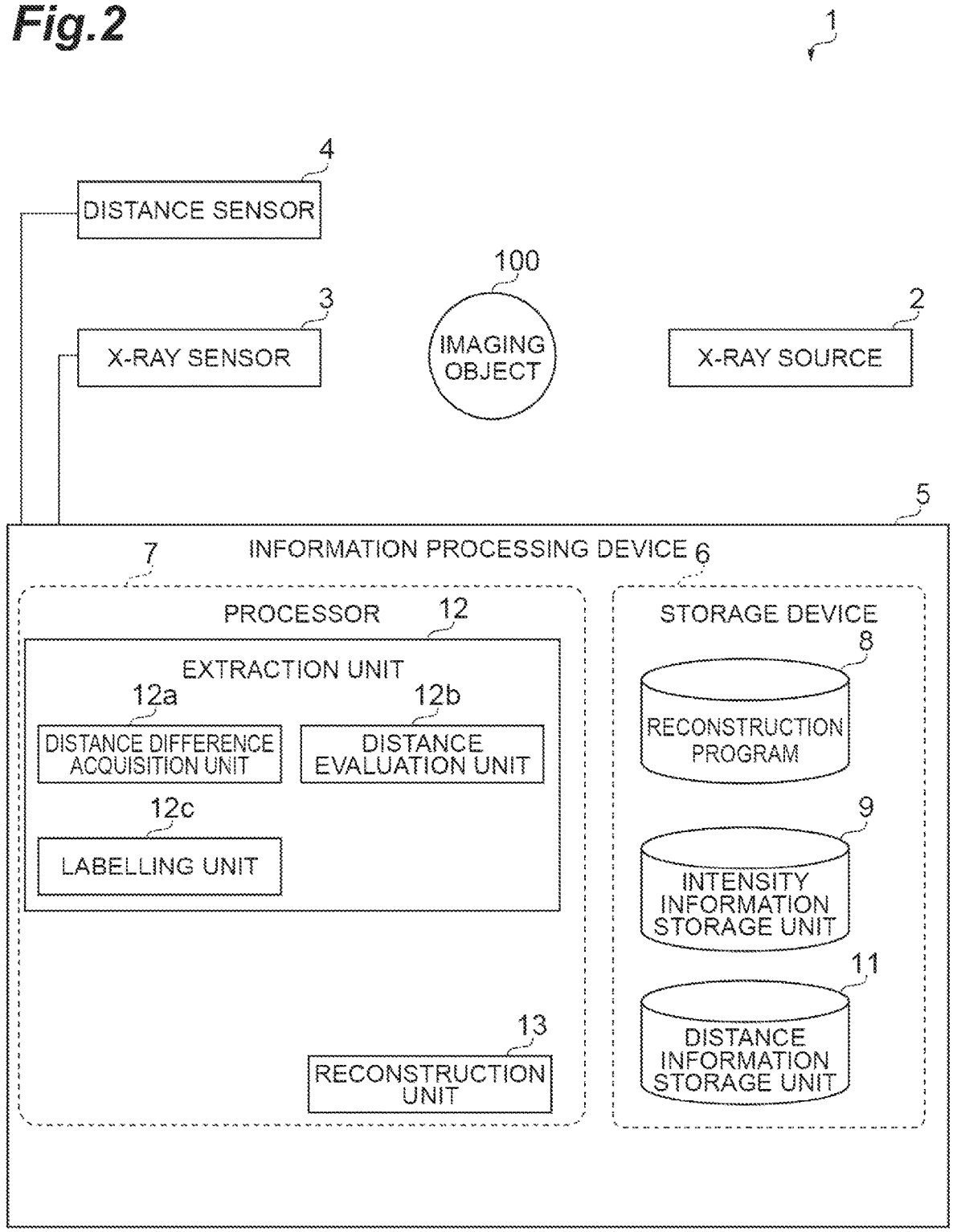
FIG. 2 is a functional block diagram of the X-ray imaging device of the first embodiment.

As illustrated in FIG. 2, physically, the information processing device 5 includes a storage device 6 and a processor 7.

For example, the storage device 6 is configured as a recording medium capable of reading/writing of data such as a random access memory (RAM), a semiconductor memory, and a hard disk device. The storage device 6 includes a reconstruction program 8, an intensity information storage unit 9, and a distance information storage unit 11.

The intensity information storage unit 9 stores the intensity information output from the X-ray sensor 3. The distance information storage unit 11 acquires the distance information output from the distance sensor 4. Information indicating timings at which the intensity information and the distance information are acquired is applied to the intensity information and the distance information, respectively. The timing information may be time or an angle with the axial line A1 set as a reference. When using the timing information, the intensity information and the distance information can be associated with each other. That is, it is possible to obtain a distance up to the imaging object 100 when acquiring arbitrary intensity information.

Note that, the information processing device 5 may process a plurality of pieces of information which are sequentially output from the X-ray sensor 3 and the distance sensor 4 in real time. In this case, the information processing device 5 may omit the intensity information storage unit 9 and the distance information storage unit 11.

Examples of the processor 7 include a central processing unit (CPU), a microcontroller, and a digital signal processor (DSP). The processor 7 may be a single process, or a multi-processor. The processor 7 functionally includes an extraction unit 12, and a reconstruction unit 13 (image generation unit). When the processor 7 reads out and executes the reconstruction program 8 stored in the storage device 6, respective functions of the extraction unit 12 and the reconstruction unit 13 are realized.

The information processing device 5 generates voxel data by using a plurality of pieces of intensity information. In a plurality of pieces of intensity information acquired at positions different from each other, an intensity difference represents the internal structure of the imaging object 100. However, even in a case where the imaging object 100 has moved or has been deformed during an intensity information acquisition period, the intensity difference occurs. Intensity information including an intensity variation that is not caused by an internal structure becomes a noise in generation of the voxel data. Here, the extraction unit 12 extracts intensity information suitable for generation of the voxel data as a reconstruction processing target.

The extraction unit 12 extracts intensity information suitable for reconstruction (hereinafter, also referred to as "composition target information") from the intensity information stored in the intensity information storage unit 9. The extraction unit 12 may receive the intensity information directly from the X-ray sensor 3. The extraction unit 12 extracts the composition target information on the basis of a state of the imaging object 100. Specifically, the extraction unit 12 evaluates a state of movement and/or deformation of the imaging object 100, and sets arbitrary information as the composition target information in a case where the state of movement and/or deformation is within an allowable range.

In addition, extraction unit 12 may output information that is not extracted as the composition target information to the storage device 6 as non-composition target information.

Hereinafter, the extraction unit 12 will be described in more detail. The extraction unit 12 includes a distance difference acquisition unit 12a, a distance evaluation unit 12b, and a labelling unit 12c. Functions thereof are realized when the processor 7 reads out and executes the reconstruction program 8.

The distance difference acquisition unit 12a reads out two pieces of distance information stored in the distance information storage unit 11. The two pieces of distance information are first distance information acquired at a first timing and second distance information acquired at a second timing. The second timing is timing after passage of predetermined time from the first timing. Note that, the timings may be treated as time, or may be treated as an angle around the axial line A1. The distance difference acquisition unit 12a obtains a distance difference that is a difference between the first distance information and the second distance information. In addition, the distance difference acquisition unit 12a outputs the distance difference to the distance evaluation unit 12b.

The distance evaluation unit 12b evaluates whether or not the distance difference is within an allowable range. When the distance difference is within the allowable range, the distance evaluation unit 12b outputs first permission information to the labelling unit 12c. On the other hand, when the distance difference is out of the allowable range, the distance evaluation unit 12b outputs first prohibition information to the labelling unit 12c.

The labelling unit 12c associates the intensity information with either permission information or prohibition information. The permission information is information indicating use for reconstruction. The prohibition information is information indicating non-use for reconstruction. Specifically, the labelling unit 12c receives the first permission information or the first prohibition information from the distance evaluation unit 12b. In addition, the labelling unit 12c reads out intensity information corresponding to the second distance information from the intensity information storage unit 9. In addition, the labelling unit 12c associates the read-out intensity information with the permission information or the prohibition information, and stores the intensity information in the intensity information storage unit 9.

The reconstruction unit 13 reads out intensity information to which the permission information is applied among a plurality of pieces of the intensity information stored in the intensity information storage unit 9. In addition, the reconstruction unit 13 performs reconstruction processing and generation of voxel data on the basis of the read-out intensity information. In the reconstruction processing and the generation of the voxel data, an arbitrary method may be used.

Figure 3:
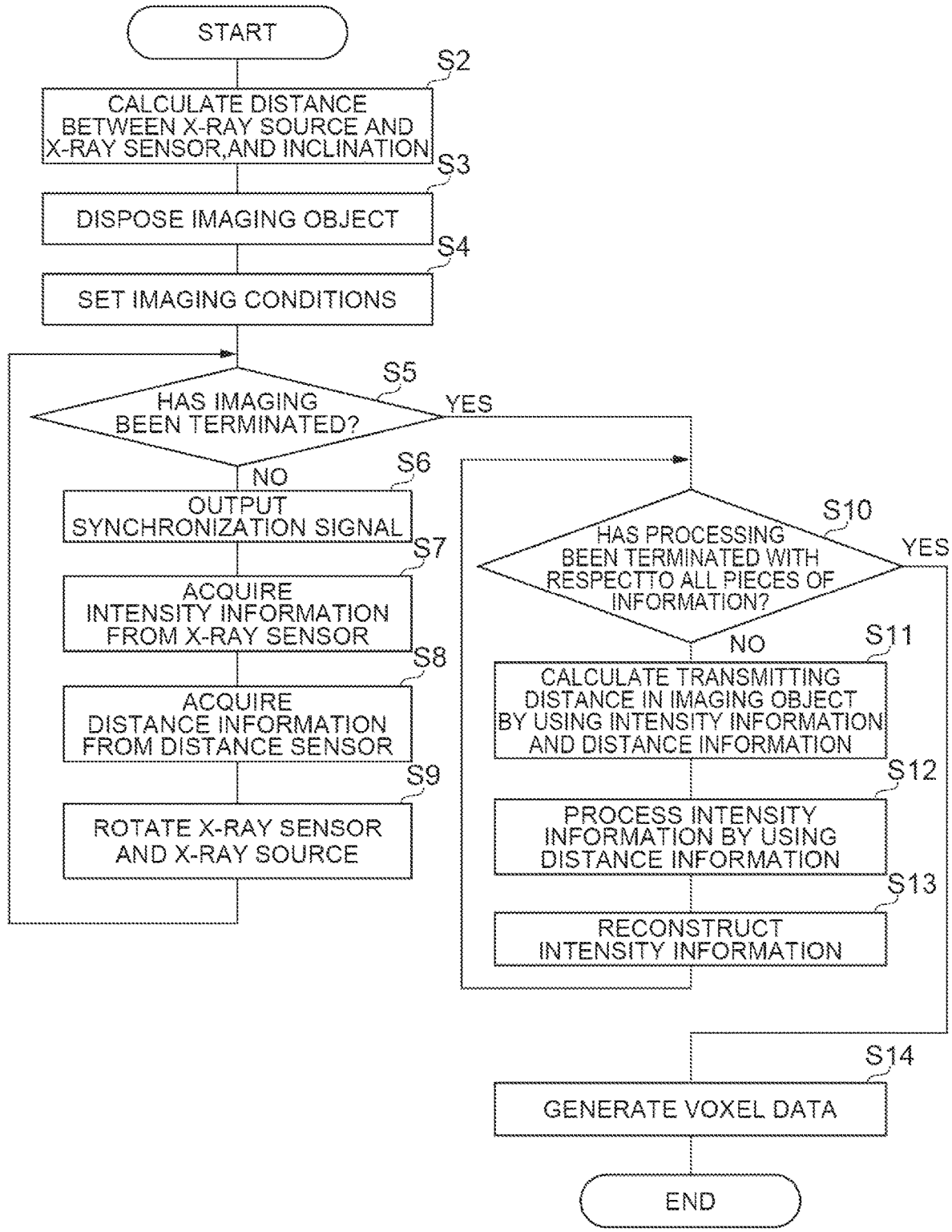
FIG. 3 is a flowchart illustrating processing performed by an information processing device.

Next, an operation of the information processing device 5 will be described with reference to FIG. 3. FIG. 3 is a flowchart illustrating a series of processing performed by the X-ray imaging device 1 illustrated in FIG. 1 and FIG. 2. The series of processing illustrated in FIG. 3 are performed for every imaging object 100.

First, a positional relationship between the X-ray source 2 and the X-ray sensor 3 is acquired (process S2). Specifically, a relative distance and an inclination of the X-ray sensor 3 with respect to the X-ray source 2 are obtained.

Next, the imaging object 100 is disposed (process S3).

Next, imaging conditions are set (process S4). Examples of the imaging conditions include a rotation speed of the X-ray source 2, the X-ray sensor 3, or the like, and the number of imaging steps.

Next, an imaging operation is performed (process S5 to process S9). The imaging operation represents an operation of acquiring the intensity information and the distance information. First, an evaluation is made as to whether or not imaging has been terminated (process S5). When imaging is not terminated (process S5: NO), the information processing device 5 outputs a synchronization signal to the X-ray source 2, the X-ray sensor, and the distance sensor 4 (process S6). Next, the information processing device 5 acquires the intensity information from the X-ray sensor 3 (process S7). Next, the information processing device 5 acquires the distance information from the distance sensor 4 (process S8). Next, the X-ray source 2, the X-ray sensor 3, and the distance sensor 4 are rotated by a predetermined angle (process S9). Then, an evaluation is made again as to whether or not imaging has been terminated (process S5). Note that, in the imaging operation, the X-ray source 2 and the X-ray sensor 3 may be fixed, and the imaging object 100 may be rotated.

When imaging is terminated (process S5: YES), the information processing device 5 performs an information processing operation (process S10 to process S14). First, the information processing device 5 evaluates whether or not processing has been terminated with respect to all pieces of information (process S10). When the processing is not terminated (process S10: NO), the information processing device 5 calculates a transmitting distance of the X-rays in the imaging object by using the intensity information and the distance information (process S11). Next, the information processing device 5 processes the intensity information by using the distance information (process S12). The intensity information processing stated herein represents association with the permission information or the prohibition information in the labelling unit 12c. That is, intensity information that is used in reconstruction of an image and intensity information that is not used in the reconstruction of the image are discriminated.

Figure 4:
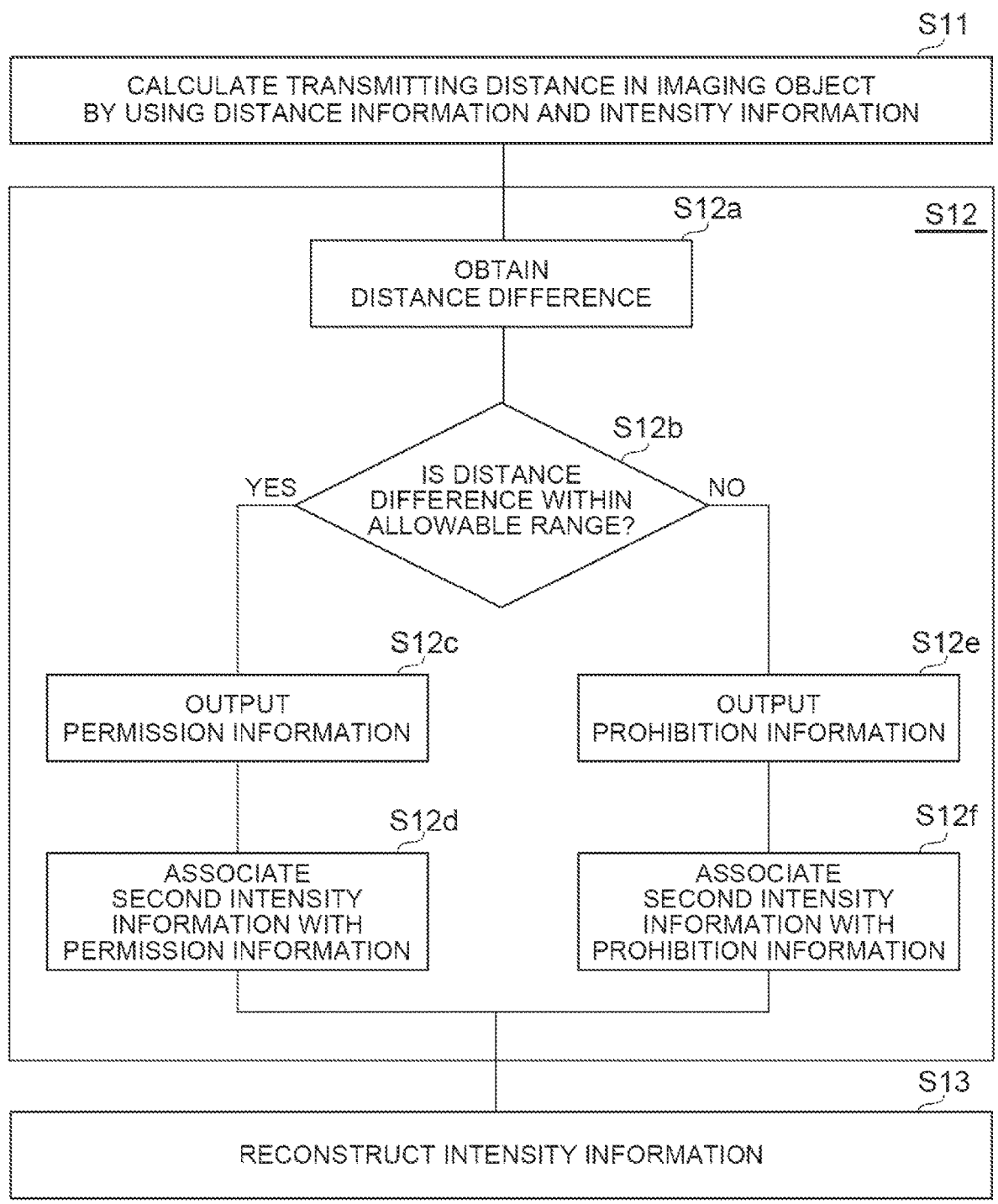
FIG. 4 is a flowchart illustrating a part of the processing performed by the information processing device in detail.

Hereinafter, the process S12 will be described in more detail with reference to FIG. 4, FIG. 5, FIG. 6, and FIG. 7. FIG. 4 is a flowchart illustrating the process S12 illustrated in FIG. 3 in more detail.

Figure 5:
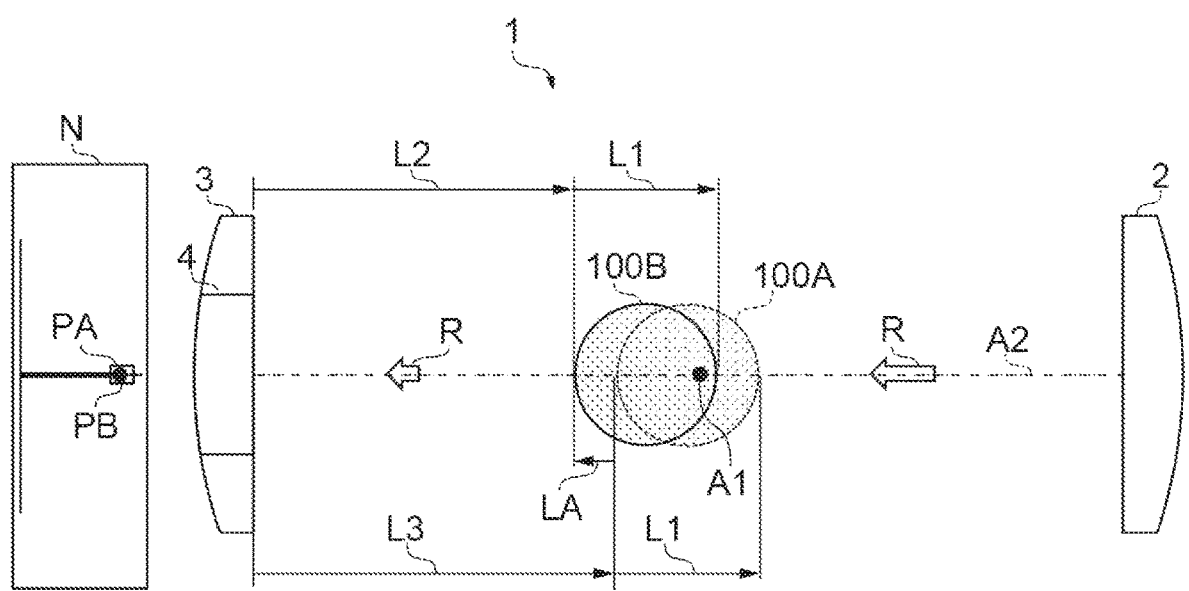
FIG. 5 is a view for describing processing in a case where an imaging object has moved.

FIG. 5 is a plan view of the X-ray imaging device 1 when viewed from the direction of the axial line A1. It is assumed that X-rays R are emitted from the X-ray source 2 along the axial line A2. The X-rays R are transmitted through an imaging object 100A. The intensity of the X-rays R after being transmitted attenuates in correspondence with an internal structure of the imaging object 100A. For example, the internal structure includes a material that constitutes the imaging object 100A, and a transmitting distance (L1) of the X-rays. In addition, the X-rays R after being transmitted are incident to the X-ray sensor 3. The X-ray sensor 3 obtains intensity of the incident X-rays R. Here, it is assumed that attenuation of the intensity of the X-rays R which occurs when being transmitted through the imaging object 100A corresponds to, for example, the material that constitutes the imaging object 100A and the transmitting distance (L1) of the X-rays. On the basis of the assumption, attenuation of the X-rays R is constant regardless of a position on the axial line A2. That is, as indicated by intensity information N, intensity (PB) of the X-rays R transmitted through an imaging object 100B located at a distance (L2) is equal to intensity (PA) of the X-rays R transmitted through the imaging object 100A located at a distance (L3). The "distance" represents a length from a light-receiving surface of the X-ray sensor 3 to a surface of the imaging object 100A or 100B on the axial line A2. That is, even though the imaging object 100A has moved to the X-ray sensor 3 side along the axial line A2 by a distance (LA), a variation is not shown in an output (intensity information) of the X-ray sensor 3. When performing reconstruction of the intensity information, when using intensity information of the imaging object 100A and intensity information of the imaging object 100B, resolution of an image obtained by reconstruction decreases.

Figure 6:
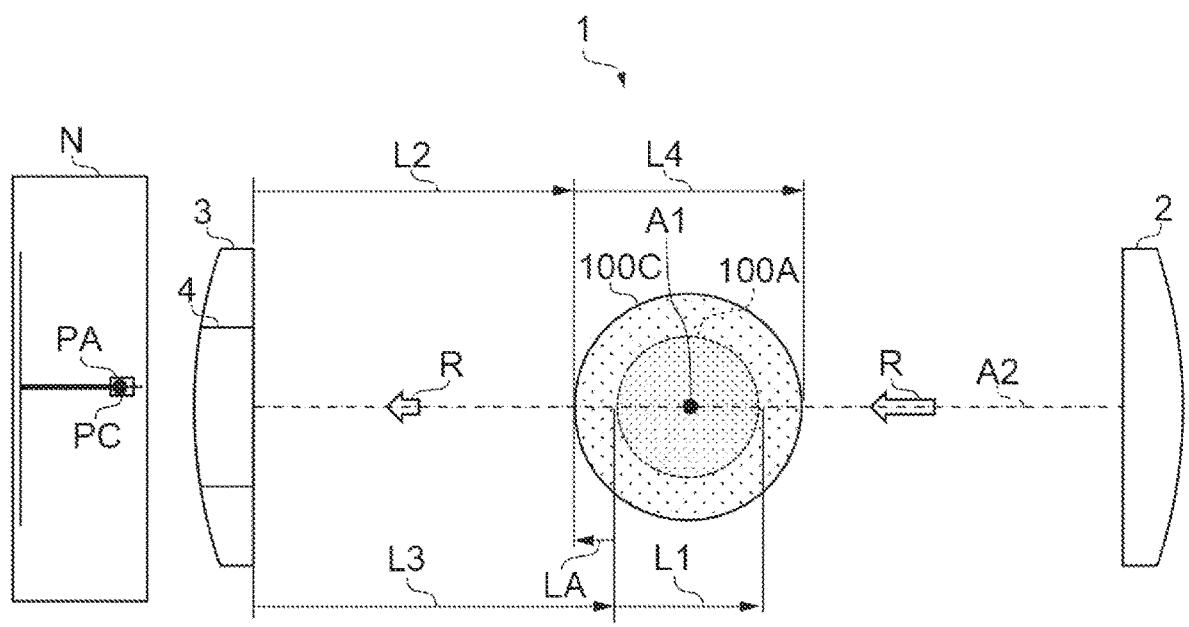
FIG. 6 is a view for describing processing in a case where the imaging object has been deformed.

Another example will be further described with reference to FIG. 6. In the above-described example, description has been given of a case where the position of the imaging object 100A or 100B in the axial line A2 varies. For example, as illustrated in FIG. 6, even in a case where the imaging object 100A has expanded and has been deformed to an imaging object 100C, the same phenomenon occurs. It is assumed that an internal configuration of the imaging object 100A or 100C is homogeneous before and after expansion. First, the X-rays R emitted to the imaging object 100A before expansion proceed through a region having a predetermined density by a transmitting distance (L1). Next, the X-rays R emitted to the imaging object 100C after expansion proceed through a region having a predetermined density by a transmitting distance (L4). When assuming that the imaging object 100C has expanded in a homogeneous manner, and a variation in a mass does not occur before and after expansion, a density after expansion is smaller than a density before expansion. On the other hand, the transmitting distance (L4) after expansion is greater than the transmitting distance (L1) before expansion in accordance with expansion. As a result, as indicated by intensity information N, intensity (PC) of the X-rays R transmitted through the imaging object 100C after expansion is the same as intensity (PA) of the X-rays R transmitted through the imaging object 100A before expansion. That is, even though the imaging object 100A has been deformed, a variation is not shown in the intensity information.

Here, the distance information is used to detect a variation of a position of the imaging object 100. As illustrated in FIG. 4, first, the distance difference acquisition unit 12a performs difference calculation (L2−L1) of the first distance (L1) and the second distance (L2) to obtain a difference distance (ΔL) (process S 12a). Next, the distance evaluation unit 12b determines whether or not the difference distance (ΔL) is within an allowable range (process S12b). For example, the allowable range may be based on the size of a pixel of a reconstruction image. When the difference distance (ΔL) is within the allowable range (process S12b: YES), the distance evaluation unit 12b outputs permission information (process S12c). The labelling unit 12c reads out second intensity information associated with the second distance from the intensity information storage unit 9. Then, the labelling unit 12c associates the second intensity information with the permission information, and stores the second intensity information in the intensity information storage unit 9 (process S12d).

On the other hand, when the difference distance (ΔL) is out of the allowable range (process S12b: NO), the distance evaluation unit 12b outputs prohibition information (process S12e). The labelling unit 12c reads out the second intensity information associated with the second distance (L2) from the intensity information storage unit 9. Then, the labelling unit 12c associates the second intensity information with the prohibition information, and stores the second intensity information in the intensity information storage unit 9 (process S12f).

As a result of execution of the above-described process S12, in a plurality of pieces of the intensity information stored in the intensity information storage unit 9, intensity information suitable for use in the reconstruction processing and intensity information that is not used in the reconstruction processing are discriminated. In other words, intensity information suitable for use in the reconstruction processing is extracted.

A phenomenon in which the distance from the X-ray sensor 3 to the imaging object 100 has varied is determined in processing in the process S12. The variation of the distance may be caused by movement of the imaging object 100 as illustrated in FIG. 5. In addition, the variation may also be caused by deformation of the imaging object 100 as illustrated in FIG. 6. In the evaluation in the process S12, it is difficult to determine that the variation of the distance is which aspect. However, even in any aspect, intensity information relating to each aspect is not suitable for use in the reconstruction processing, and thus is excluded so as not to be used in the reconstruction processing.

Figure 7:
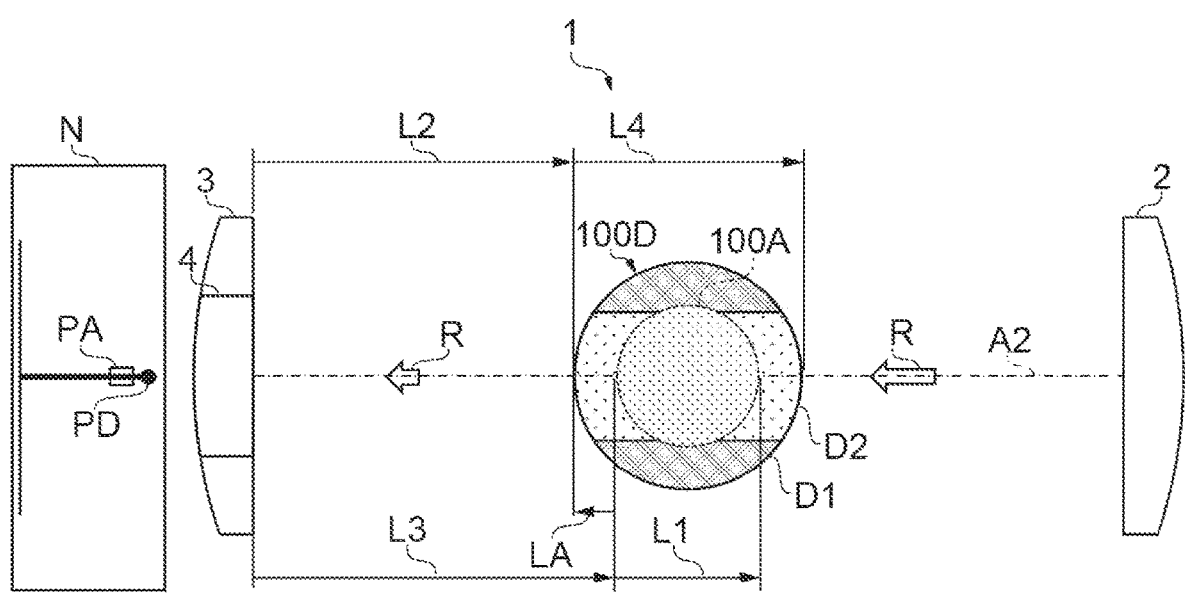
FIG. 7 is a view for describing processing in a case where the imaging object has been deformed in another aspect.

Note that, in FIG. 6, it is assumed that expansion of the imaging object 100C is homogeneous. For example, "homogeneous" stated herein represents that a density distribution of the imaging object 100C does not vary before and after expansion. Note that, a value of the density varies before and after expansion. For example, as illustrated in FIG. 7, in a case where expansion of the imaging object 100D is not homogeneous, a difference occurs in the attenuation of the X-rays R. For example, "not homogeneous" stated herein represents that a density distribution of the imaging object 100D has varied before and after expansion. That is, a density distribution of the imaging object 100A before expansion is constant. However, the density distribution of the imaging object 100D after expansion is not constant. That is, the imaging object 100D includes a high-density portion D1 and a low-density portion D2. For example, the intensity (PD) of the X-rays R transmitted through the imaging object 100D after expansion may vary with respect to the intensity (PA) of the X-rays R transmitted through the imaging object 100A before expansion. In this case, it is possible to determine that non-homogeneous expansion occurs in the imaging object 100D by using the distance information and the intensity information.

Note that, in description of the embodiment, a variation aspect in which a difference does not occur in the intensity information is defined as "first aspect". In addition, a variation aspect in which a difference occurs in the intensity information is defined as "second aspect". The "intensity information" stated herein represents peak intensity in an intensity distribution indicated by the intensity information. Accordingly, in the first aspect, even in a case where a difference does not exist in the peak intensity, a difference may occur in the intensity distribution. This aspect will be described later in detail.

Description will be made with reference to FIG. 3 again. The information processing device 5 performs reconstruction processing by using the intensity information to which the permission information is applied. Then, the information processing device 5 evaluates again whether or not processing has been terminated with respect to all pieces of information (process S10). When the processing is terminated (process S10: YES), the information processing device 5 generates voxel data (process S14). A plurality of pieces of reconstruction information are used in the generation of the voxel data.

However, the radiation detector is used in inspection for medical treatment, industry, security, and industrial infrastructures, inspection for social infrastructure, or the like. The radiation detector can image internal information non-destructively, and the radiation detector is widely used in the fields. For example, as an application example of the radiation detector, a computed tomography is exemplified. The computed tomography can obtain a three-dimensional tomographic image. In the tomographic image of the computed tomography, a state in which the imaging object 100 is fixed is an ideal state. That is, in a case where the imaging object is fixed during imaging, theoretically maximum resolution can be obtained.

However, the imaging object 100 including a human being may not be a rigid body. For example, in the case of a living body, there is also a movement that cannot be stopped. As a result, resolution decreases in accordance with movement of the imaging object 100. Accordingly, the capability of the X-ray sensor 3 cannot be sufficiently exhibited. For example, a medical computed tomography solves the problem by rotating a gantry including an X-ray source and an X-ray sensor at a high speed. Specifically, it is assumed that the imaging object is a human being. The human being breathes during imaging, and thus movement according to breathing occurs. Here, the medical computed tomography rotates the gantry at a rotation speed of approximately three rotations per second. On the other hand, the gantry is a heavy object, a drive device of the gantry has a large size.

The X-ray imaging device 1 of the embodiment evaluates movement of the imaging object 100 by the distance sensor 4. As a result, the number of rotations of the X-ray source 2 and the X-ray sensor 3 is not increased, and thus a decrease in resolution can be suppressed. In addition, the X-ray imaging device 1 of this embodiment can capture an image at a high frame rate such as 30 frames per second (FPS) or 60 FPS. As a result, even in a case where the imaging object 100 moves or deforms at a high speed, a satisfactory tomographic image can be obtained.

The above-described effect is obtained because a distance between the X-ray sensor 3 and the imaging object 100 is evaluated by the distance sensor 4. For example, when using a ToF camera as the distance sensor 4, it is possible to obtain a two-dimensional image including the distance information at a high frame rate. Here, the distance sensor 4 obtains the distance information up to the imaging object 100 in synchronization with a timing at which the X-ray sensor 3 acquires the intensity information. As a result, in the case of performing reconstruction of an image by using the intensity information, when using the distance information, it is possible to exclude intensity information that is not suitable for the reconstruction. In addition, the intensity information can also be corrected on the basis of the distance information. As a result, a decrease in resolution is suppressed, and thus the performance of the X-ray sensor 3 can be sufficiently exhibited.

In short, the information processing device 5 of the X-ray imaging device 1 extracts information that is used in generation of imaging information from the intensity information by using the distance information. The distance information shows a relative positional relationship between the X-ray sensor 3 and the imaging object 100. Accordingly, the information processing device 5 can extract intensity information suitable for generation of imaging information on the basis of the distance information. That is, in a case where the imaging object 100 has moved, intensity information suitable for reconstruction is selected. As a result, deterioration of the quality of the imaging information is suppressed. In other words, a decrease in the resolution is suppressed. Accordingly, the performance of the X-ray sensor 3 can be sufficiently drawn out.

Second Embodiment

In the X-ray imaging device 1 of the first embodiment, intensity information obtained under inappropriate conditions is excluded from the reconstruction processing on the basis of the distance information. However, even in the intensity information obtained under the inappropriate conditions, when a variation aspect of the imaging object 100 can be specified, the intensity information may be suitable for use in the reconstruction processing by performing correction processing. An X-ray imaging device 1A of a second embodiment is different from the X-ray imaging device 1 of the first embodiment in that intensity information correction processing is included. Hereinafter, the X-ray imaging device 1A of the second embodiment will be described with reference to FIG. 8, FIG. 9, FIG. 10, FIG. 11, and FIG. 12. In the following description, description of a configuration common to the X-ray imaging device 1 of the first embodiment will be omitted. In addition, a configuration different from the X-ray imaging device 1 of the first embodiment will be described in detail.

Figure 8:
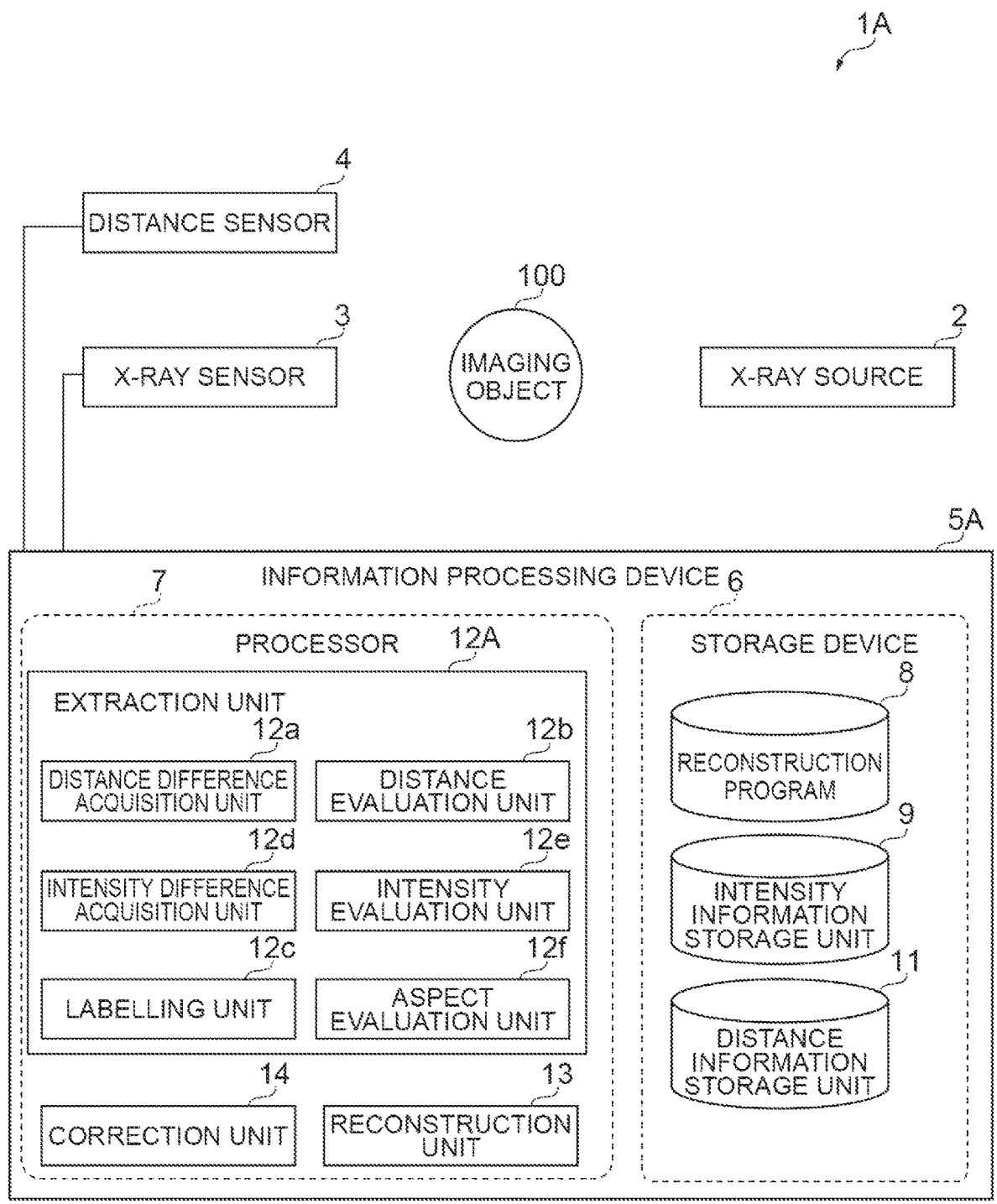
FIG. 8 is a functional block diagram of an X-ray imaging device of a second embodiment.

As illustrated in FIG. 8, the X-ray imaging device 1A includes an information processing device 5A. The information processing device 5A includes an extraction unit 12A. The extraction unit 12A further includes an intensity difference acquisition unit 12d, an intensity evaluation unit 12e, an aspect evaluation unit 12f, and a correction unit 14 in addition to the distance difference acquisition unit 12a, the distance evaluation unit 12b, the labelling unit 12c, and the reconstruction unit 13.

The intensity difference acquisition unit 12d obtains a difference between first peak intensity in first intensity information and second peak intensity in second intensity information.

The intensity evaluation unit 12e acquires a first full width at half maximum that represents an intensity distribution in the first intensity information. In addition, the intensity evaluation unit 12e acquires a second full width at half maximum that represents an intensity distribution in the second intensity information. In addition, the intensity evaluation unit 12e evaluates a magnification relationship between the first full width at half maximum and the second full width at half maximum.

The aspect evaluation unit 12f evaluates an aspect of the imaging object 100 on the basis of a result in the distance evaluation unit 12b and a result in the intensity evaluation unit 12e. The aspect of the imaging object 100 includes movement and deformation of the imaging object 100. In addition, the movement of the imaging object 100 includes approaching movement toward the X-ray sensor 3 and separation movement away from the X-ray sensor 3. Note that, the movement of the imaging object 100 may include parallel movement with respect to a light-receiving surface of the X-ray sensor 3. The deformation of the imaging object 100 includes expansion of the imaging object 100 and contraction of the imaging object 100. It is assumed that a variation of the aspects is homogeneous.

An operation of the aspect evaluation unit 12f will be described in detail. As described already with reference to FIG. 5, in the movement of the imaging object 100 on the axial line A1, a variation is not shown in the intensity information. In addition, as described with reference to FIG. 6, in the homogeneous deformation of the imaging object 100, a variation is not shown in the intensity information. Here, the variation of the intensity information stated herein represents a variation of peak intensity in an intensity distribution indicated by the intensity information.

Figure 9:
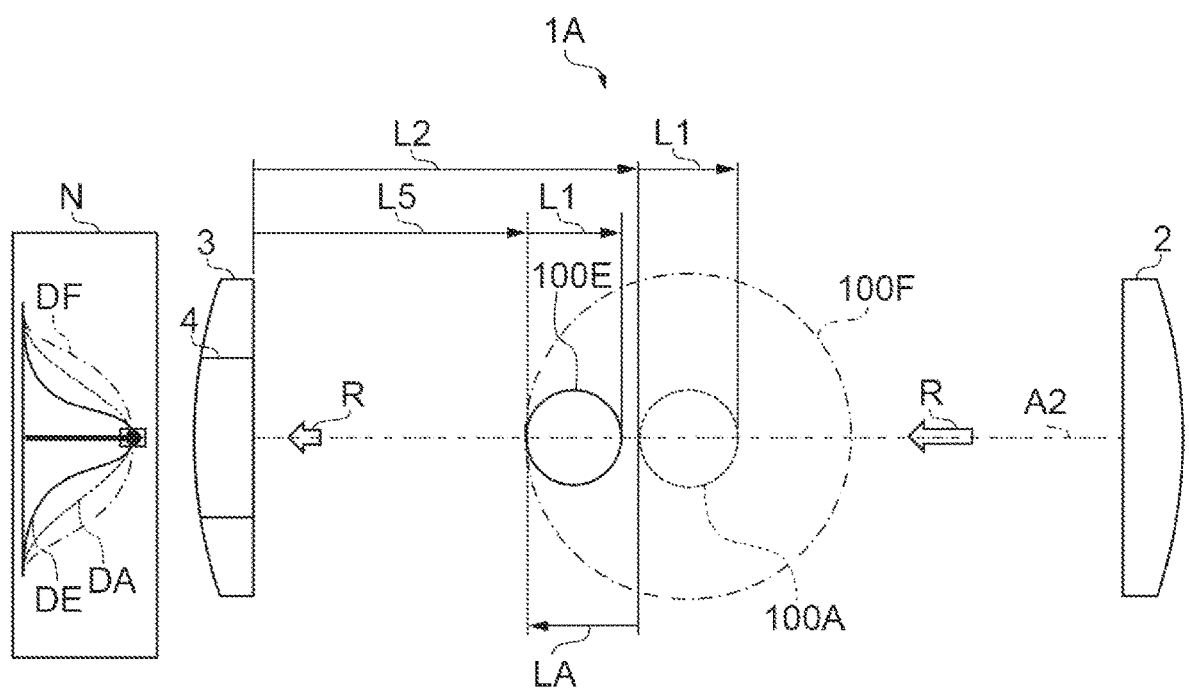
FIG. 9 is a view for describing a method of determining an aspect of an imaging object.

For example, as illustrated in FIG. 9, when the distance information indicates that the distance between the X-ray sensor 3 and a surface of an imaging object 100E or 100F has decreased, the imaging object 100A may move toward the X-ray sensor 3 to be imaging object 100E. In addition, the imaging object 100A may expand without variation of the position of the imaging object 100, and may become the imaging object 100F. However, it is difficult to determine the two cases with only peak intensity.

On the other hand, attention is paid to intensity information N illustrated in FIG. 9. An intensity distribution DE (of the imaging object 100E) in a case where the imaging object 100A has moved toward the X-ray sensor 3 is different from an intensity distribution DA of the imaging object 100A. In addition, an intensity distribution DF (of the imaging object 100F) in a case where the imaging object 100A has expanded is different from the intensity distribution DA of the imaging object 100A. In addition, the intensity distribution DE in the case of approaching movement toward the X-ray sensor 3 is also different from the intensity distribution DF in the case of expansion. Accordingly, when the distance information indicates that the distance has been shortened, it is possible to determine whether this state is approaching movement toward the X-ray sensor 3 or expansion by evaluating the intensity distributions DA, DE, and DF. For example, a full width at half maximum may be used in the evaluation of the intensity distributions DA, DE, and DF. Specifically, when the full width at half maximum has decreased, evaluation can be made as approaching movement toward the X-ray sensor 3. On the other hand, when the full width at half maximum has increased, evaluation can be made as expansion.

Figure 10:
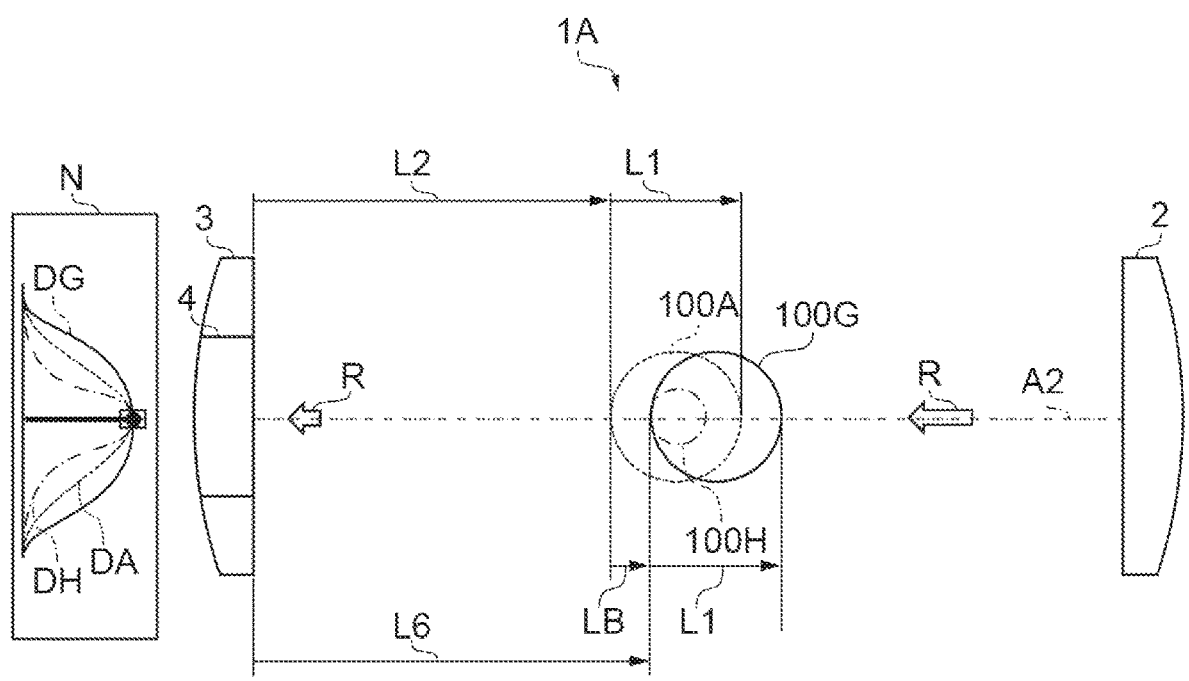
FIG. 10 is a view for describing a method of determining the aspect of the imaging object.
Figure 11:
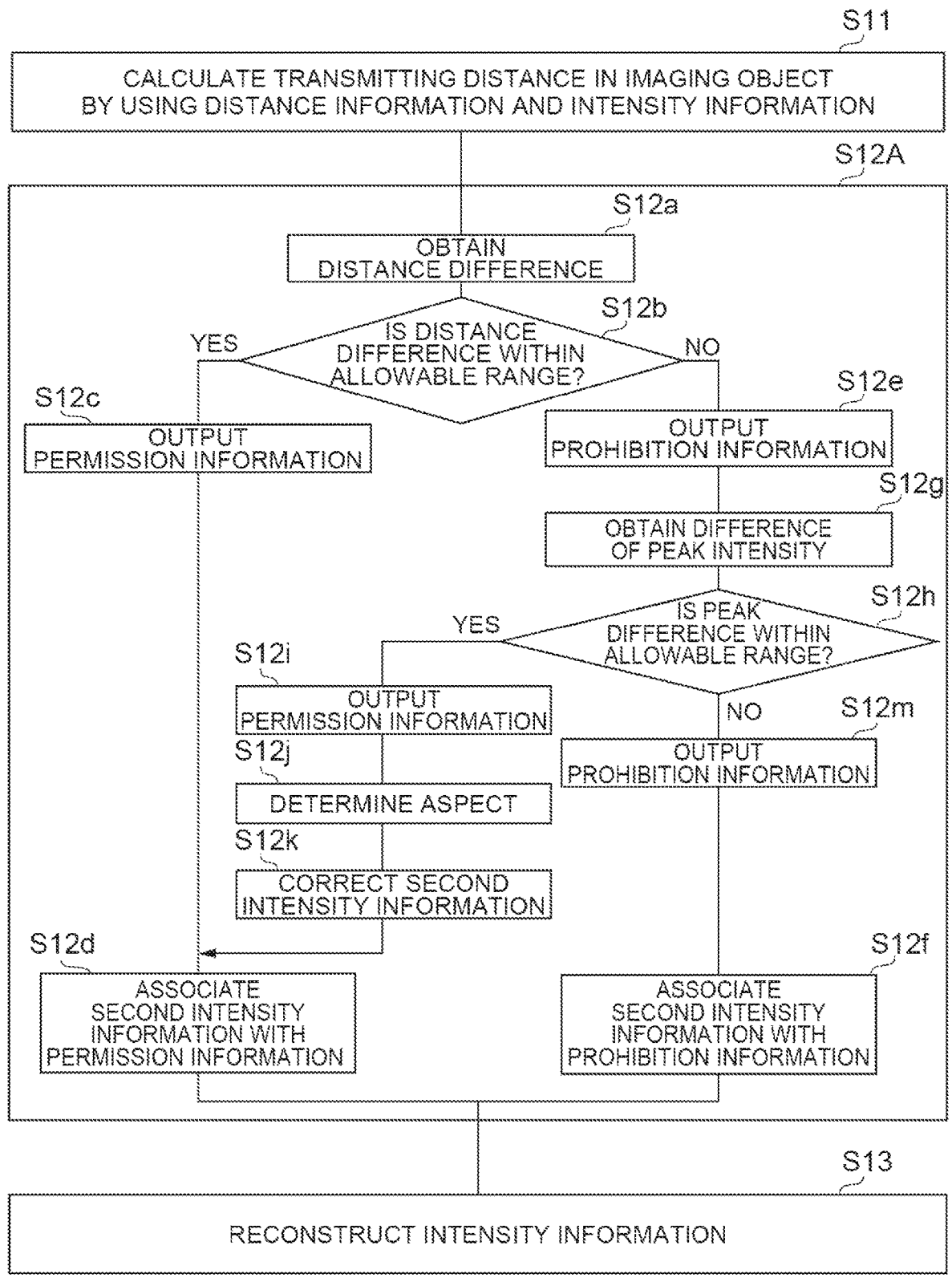
FIG. 11 is a flowchart illustrating a part of processing performed by an information processing device of the X-ray imaging device of the second embodiment in detail.

As illustrated in FIG. 10, the distance information may also indicate that a distance between the X-ray sensor 3 and a surface of an imaging object 100G or 100H has increased. For example, it is assumed that the distance from the X-ray sensor 3 to the surface of the imaging object 100G or 100H has varied from a distance L2 to a distance L6. In this case, it is determined whether an increase in a distance LB is caused by movement or deformation of the imaging object. That is, either movement or deformation of the imaging object 100A is determined on the basis of an increase or a decrease in the full width at half maximum. Specifically, as shown in an intensity distribution DH of the imaging object 100H, when the full width at half maximum has decreased further than the full width at half maximum of the intensity distribution DA of the imaging object 100A, evaluation is made as contraction. On the other hand, as shown in an intensity distribution DG of the imaging object 100, when the full width at half maximum has increased further than the full width at half maximum of the intensity distribution DA of the imaging object 100A, evaluation is made as separation movement away from the X-ray sensor 3.

The correction unit 14 corrects the second intensity information on the basis of a result in the aspect evaluation unit 12f. The result of the aspect evaluation unit 12f represents that the aspect of the imaging object 100 is any one of approaching movement, separation movement, expansion, and contraction. The correction unit 14 corrects the intensity information by using a magnification rate relating to the X-rays emitted from the X-ray source 2, or the like in correspondence with four aspects.

The X-ray imaging device 1A carries out a process S12A in substitution for the process S12 illustrated in the flowchart of FIG. 4. Hereinafter, the process S12A carried out by the X-ray imaging device 1A will be described in detail with reference to FIG. 11 and FIG. 12.

First, the distance difference acquisition unit 12a obtains a distance difference (process S12a). Next, the distance evaluation unit 12b evaluates whether or not the distance difference is within an allowable range (process S12b). When the distance difference is within the allowable range, the distance evaluation unit 12b outputs permission information (process S12c). Then, the labelling unit 12c associates the second intensity information with the permission information (process S12d). As described above, the processes S12a, S12b, S12c, and S12d are the same as in the operation of the X-ray imaging device 1 of the first embodiment.

On the other hand, the X-ray imaging device 1A of the second embodiment includes processing different from the X-ray imaging device 1 of the first embodiment in processing when the distance difference is within the allowable range.

The distance evaluation unit 12b outputs the distance difference to the aspect evaluation unit 12f. The distance difference is a positive or negative integral. For example, the distance difference that is a positive integral represents that a distance from the X-ray sensor 3 to the surface of the imaging object 100 is shortened. On the other hand, the distance difference that is a negative integral represents that the distance from the X-ray sensor 3 to the surface of the imaging object 100 is lengthened. Note that, a relationship between the positive and the negative of the distance difference, and the approaching and remoteness of the imaging object 100 may be set in an arbitrary manner.

First, when the distance difference is out of the allowable range (process S12b: NO), the distance evaluation unit 12b outputs prohibition information (process S12e).

Next, the intensity difference acquisition unit 12d obtains a difference of peak intensity (process S12g). Specifically, first, the intensity difference acquisition unit 12d reads out the first intensity information relating to the first timing and the second intensity information relating to the second timing from the intensity information storage unit 9. The first intensity information and the second intensity information have a one-dimensional distribution. The intensity difference acquisition unit 12d extracts the first peak intensity from an intensity distribution indicated by the first intensity information. In addition, the intensity difference acquisition unit 12d extracts the second peak intensity from an intensity distribution indicated by the second intensity information. In addition, the intensity difference acquisition unit 12d obtains a peak difference between the first peak intensity and the second peak intensity.

Next, the intensity evaluation unit 12e evaluates whether or not the peak difference is within an allowable range (process S12h). In the process S12h, in a case where the distance difference is within the allowable range, a determination is made as to whether or not the intensity distribution can be corrected. For example, movement of the imaging object 100 can be corrected by predetermined calculation. Similarly, homogeneous expansion or contraction of the imaging object 100 can also be corrected.

In the movement of the imaging object 100B illustrated in FIG. 5 and the homogeneous deformation of the imaging object 100C illustrated in FIG. 6, a variation of the peak intensity substantially does not occur. On the other hand, in the non-homogeneous deformation of the imaging object 100D illustrated in FIG. 7, a variation of the peak intensity occurs. Accordingly, a determination is made as to whether or not the aspect is a correctable aspect in accordance with whether or not the difference of the peak intensity is within the allowable range.

When the difference of the peak intensity is out of the allowable range (process S12h: NO), the intensity evaluation unit 12e outputs prohibition information (process S12m). Then, the labelling unit 12c associates the second intensity information with the prohibition information (process S12f).

When the difference of the peak intensity is within the allowable range (process S12h: YES), the intensity evaluation unit 12e outputs permission information (process S12i). Continuously, the aspect evaluation unit 12f evaluates the aspect of the imaging object 100 (process S12j).

Figure 12:
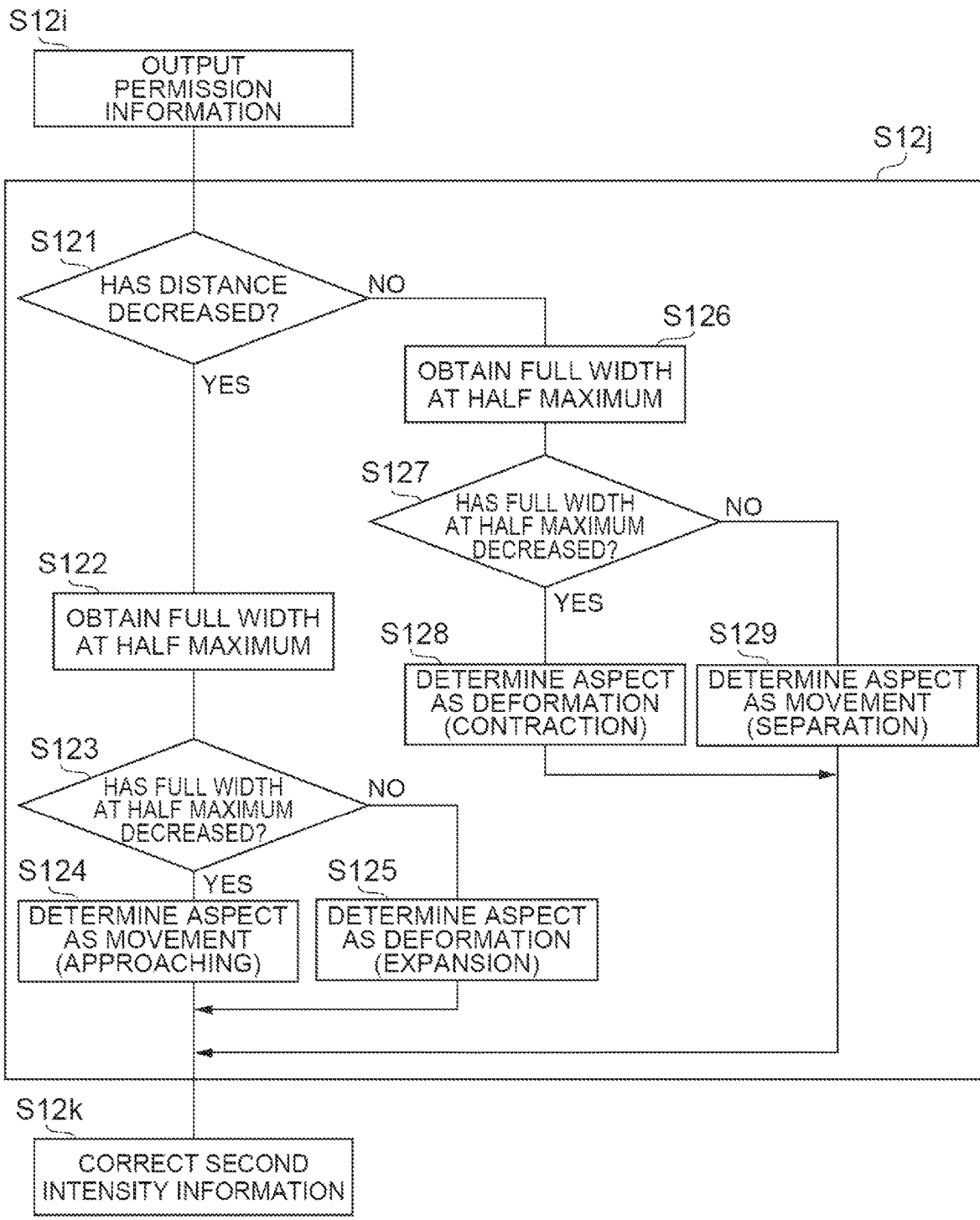
FIG. 12 is a flowchart illustrating a part of the processing performed by the information processing device of the X-ray imaging device of the second embodiment in more detail.

Details of the process S12j will be described with reference to FIG. 12.

First, the aspect evaluation unit 12f obtains the distance difference from the distance difference acquisition unit 12a. Then, the aspect evaluation unit 12f determines whether or not the distance from the X-ray sensor 3 to the imaging object 100 has decreased on the basis of the distance difference (process S121). When the distance has decreased (process S121: YES), the aspect evaluation unit 12f obtains the first full width at half maximum of the first intensity distribution which is indicated by the first intensity information (process S122). The aspect evaluation unit 12f obtains the second full width at half maximum of the second intensity distribution which is indicated by the second intensity information (process S122). Continuously, the aspect evaluation unit 12f obtains a difference between the first full width at half maximum and the second full width at half maximum.

Then, the aspect evaluation unit 12f evaluates whether or not the full width at half maximum has decreased on the basis of the difference (process S123). When the full width at half maximum has decreased (process S123: YES), the aspect evaluation unit 12f evaluates the aspect of the imaging object 100 as approaching movement toward the X-ray sensor 3 (process S124). On the other hand, when the full width at half maximum has increased (process S123: NO), the aspect evaluation unit 12f evaluates the aspect of the imaging object 100 as expansion (process S125).

On the other hand, when the distance has increased (process S121: NO), the aspect evaluation unit 12f performs the same processing as in the process S122. That is, the aspect evaluation unit 12f obtains the difference between the first full width at half maximum and the second full width at half maximum. Then, the aspect evaluation unit 12f evaluates whether or not the full width at half maximum has decreased on the basis of the difference (process S127). When the full width at half maximum has decreased (process S127: YES), the aspect evaluation unit 12f evaluates the aspect of the imaging object 100 as contraction (process S128). On the other hand, when the full width at half maximum has increased (process S127: NO), the aspect evaluation unit 12f evaluates the aspect of the imaging object 100 as separation movement away from the X-ray sensor 3 (process S129).

Description will be made with reference to FIG. 11 again. The correction unit 14 performs correction of the second intensity information on the basis of the result in the process S12*j* (process S12*k*). Continuously, the labelling unit 12*c* associates the second intensity information after correction with the permission information. Then, the labelling unit 12*c* stores the second intensity information to which the permission information is applied in the intensity information storage unit 9.

According to the X-ray imaging device 1A of the second embodiment, intensity information suitable for reconstruction of an image can be extracted as in the X-ray imaging device 1 of the first embodiment. Accordingly, deterioration of the quality of the reconstruction information can be suppressed.

In addition, the X-ray imaging device 1A of the second embodiment extracts intensity information that is correctable among a plurality of pieces of intensity information which are not suitable for reconstruction of an image. In addition, the intensity information is corrected to convert the intensity information into intensity information suitable for reconstruction. As a result, the number of pieces of the intensity information capable of being used in reconstruction increases, and thus the quality of the reconstruction information can be improved.

The X-ray imaging device of the present invention is not limited to the above-described embodiments, and various modifications can be made within a range not departing from the gist of the present invention.

REFERENCE SIGNS LIST

1: X-ray imaging device, 2: X-ray source, 3: X-ray sensor (X-ray intensity measurement unit), 4: distance sensor (distance measurement unit), 5: information processing device (information processing unit), 6: storage device, 7: processor, 8: reconstruction program, 9: intensity information storage unit, 10: measurement light, 11: distance information storage unit, 12: extraction unit, 13: reconstruction unit, 14: correction unit, 12*a*: distance difference acquisition unit, 12*b*: distance evaluation unit, 12*c*: labelling unit, 12*d*: intensity difference acquisition unit, 12*e*: intensity evaluation unit, 12*f*: aspect evaluation unit.

The invention claimed is:

1. An X-ray imaging device that obtains imaging information indicating an internal structure of an imaging object by using intensity of X-rays transmitted through the imaging object, comprising:
   an X-ray source that emits the X-rays toward the imaging object;
   an X-ray intensity measurement unit that is disposed to face the X-ray source with the imaging object interposed therebetween, and obtains intensity information of the X-rays transmitted through the imaging object;
   a distance measurement unit that irradiates the imaging object with measurement light reflected from a surface of the imaging object, and obtains distance information to the surface of the imaging object by using the measurement light reflected from the surface of the imaging object; and
   an information processing unit that obtains the imaging information by using the intensity information and the distance information,
   wherein the information processing unit includes,
   an extraction unit that extracts information used in generation of the imaging information from a plurality of pieces of the intensity information by using at least the distance information, and
   an image generation unit that generates the imaging information by using the intensity information extracted in the extraction unit, and
   the extraction unit includes,
   a distance difference acquisition unit that acquires a distance difference between first distance information acquired at a first timing and second distance information acquired at a second timing,
   a distance evaluation unit that evaluates whether or not the distance difference is within an allowable range, and outputs first permission information when the distance difference is within the allowable range, and
   a labelling unit that applies information indicating use for generation of the imaging information to the intensity information acquired at the second timing when the output of the distance evaluation unit is the first permission information.

2. The X-ray imaging device according to claim 1,
   wherein the distance evaluation unit outputs first prohibition information when the distance difference is not within the allowable range, and
   the extraction unit further includes,
   an intensity difference acquisition unit that acquires an intensity difference between first intensity information acquired at the first timing and second intensity information acquired at the second timing,
   an intensity evaluation unit that evaluates whether or not the intensity difference is within an allowable range, outputs second permission information when the intensity difference is within the allowable range, and outputs second prohibition information when the intensity difference is not within the allowable range, and
   an aspect evaluation unit that evaluates that a variation in a first aspect has occurred in the imaging object when the output of the distance evaluation unit is the first prohibition information and the output of the intensity evaluation unit is the second permission information, and evaluates that a variation in a second aspect has occurred in the imaging object when the output of the distance evaluation unit is the first prohibition information and the output of the intensity evaluation unit is the second prohibition information.

3. The X-ray imaging device according to claim 2,
   wherein the X-ray intensity measurement unit acquires intensity distributions of the X-rays which are emitted from the X-ray source and are transmitted through the imaging object as the first intensity information and the second intensity information, and
   the aspect evaluation unit determines that the first aspect is either a deformation of the imaging object or movement of the imaging object in correspondence with a comparison result between the intensity distribution indicated by the first intensity information and the intensity distribution indicated by the second intensity information.

* * * * *